(12) United States Patent
Zagorchev et al.

(10) Patent No.: US 9,265,590 B2
(45) Date of Patent: Feb. 23, 2016

(54) MULTIMODAL IMAGING FIDUCIAL MARKER

(75) Inventors: Lyubomir Zagorchev, Lebanon, NH (US); Douglas Stanton, Ossining, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1079 days.

(21) Appl. No.: 12/995,687

(22) PCT Filed: May 29, 2009

(86) PCT No.: PCT/IB2009/052286
§ 371 (c)(1),
(2), (4) Date: Dec. 2, 2010

(87) PCT Pub. No.: WO2009/150564
PCT Pub. Date: Dec. 17, 2009

(65) Prior Publication Data
US 2011/0105896 A1    May 5, 2011

Related U.S. Application Data

(60) Provisional application No. 61/061,154, filed on Jun. 13, 2008.

(51) Int. Cl.
*A61B 6/00* (2006.01)
*A61B 19/00* (2006.01)
*A61B 6/03* (2006.01)

(52) U.S. Cl.
CPC ............... *A61B 19/54* (2013.01); *A61B 6/508* (2013.01); *A61B 6/037* (2013.01); *A61B 2019/5287* (2013.01); *A61B 2019/5289* (2013.01); *A61B 2019/542* (2013.01); *A61B 2019/5495* (2013.01)

(58) Field of Classification Search
CPC ............ A61B 19/54; A61B 2019/5287; A61B 2019/5289; A61B 2019/542; A61B 2019/5495; A61B 6/037; A61B 6/508
See application file for complete search history.

(56) References Cited

U.S. PATENT DOCUMENTS

| | | |
|---|---|---|
| 5,469,847 A | 11/1995 | Zinreich et al. |
| 5,702,128 A | 12/1997 | Maxim et al. |
| 2004/0064011 A1 | 4/2004 | Grabowy et al. |
| 2005/0119562 A1 | 6/2005 | Jones et al. |
| 2006/0173280 A1* | 8/2006 | Goosen et al. ................. 600/414 |
| 2007/0110665 A1 | 5/2007 | Bolan et al. |
| 2008/0009718 A1* | 1/2008 | Zohman ........................ 600/426 |

FOREIGN PATENT DOCUMENTS

| | | |
|---|---|---|
| CN | 2574602 Y | 9/2003 |
| CN | 101048112 A | 10/2007 |
| EP | 1579878 A1 | 9/2005 |
| WO | 0024332 A1 | 5/2000 |
| WO | 0108578 A1 | 2/2001 |
| WO | 2006049911 A1 | 5/2006 |
| WO | 2007019113 A2 | 2/2007 |
| WO | 2007045913 A2 | 4/2007 |

* cited by examiner

*Primary Examiner* — Ruth S Smith

(57) ABSTRACT

A multimodal fiducial marker (10) for registration of data is disclosed. The multimodal fiducial marker (10) generally comprises a first portion (12) made from at least one radiopaque material and a second portion (14) made from a porous material capable of absorbing at least one radioactive material. The second portion (14) at least partially surrounds the first portion (12).

13 Claims, 2 Drawing Sheets

MULTIMODAL IMAGING FIDUCIAL MARKER

CROSS REFERENCE TO RELATED APPLICATIONS

This application claims the benefit of U.S. provisional application Ser. No. 61/061,154 filed Jun. 13, 2008, which is incorporated herein by reference.

The present application generally relates to the imaging arts and more particularly to image registration. Image registration is the process of spatially aligning images of the same or different subjects. Image registration has many applications. For example, in investigation of in-vivo models of disease, multimodal imaging of the same or groups of different animals may be required. In these studies, the scans taken using various different imaging modalities provide complementary information, or data, that is utilized to identify, compare, and track progression of disease. This information can be registered such that the acquired images are aligned in a common coordinate frame for validation of results, planning, navigation, diagnosis, and for other purposes. Such imaging modalities may include computed tomography ("CT"), fluoroscopy, positron emission tomography ("PET"), micro PET, single photon emission computed tomography ("SPECT"), micro SPECT, magnetic resonance ("MR"), ultrasound, and others.

Existing image registration techniques can be classified into two groups: rigid registration and nonrigid registration. Rigid registration involves the alignment of objects that do not change shape or deform locally. In rigid registration, two images are brought into spatial alignment by transformation of the Cartesian coordinate system. The registration is represented by a rigid linear transformation matrix, which is used to remove the global difference in position and orientation between two objects. Nonrigid registration involves the alignment of objects that can change shape or deform locally. As such, the images can be aligned by a non-linear transformation.

Registration of multimodal imaging data is a complex process involving both rigid and nonrigid image registration. The complexity is due to the lack of conspicuous anatomical features or structures of the imaged subject(s) in different modalities. For example, registering multimodal data in small animals, such as mice or rats, is especially complex. That complexity results from the small size of the imaging targets and the high sensitivity and spatial resolution of the imaging hardware. Due to those factors, very small movements of the subject between imaging scans can have a large impact on registering the images.

Algorithms for rigid image registration range from fully manual to fully automatic. The most reliable, accurate, and robust algorithms for rigid image registration are usually based on point landmarks or fiducial markers. These algorithms calculate the coefficients of the transformation matrix based on the point coordinates of corresponding fiducials (landmarks) in the multiple images to be registered. Assuming that fiducials can be easily identified and their location determined, the output of such algorithms provide for accurate rigid image registration.

In the present application, the design and a method of use of an easily identifiable multimodal fiducial marker for registration of multimodal data is described. The multimodal fiducial marker of the present application generally includes two portions. A first portion comprises at least one radiopaque material, which may be detected by CT, fluoroscopy, MR, and ultrasound imaging. A second portion comprises a porous material capable of absorbing at least one high density radioactive material, which may be detected by PET, micro PET, SPECT, and micro SPECT imaging. The second portion may at least partially surround the first portion. However, the invention may take form in various components and arrangements of components.

The described multimodal fiducial marker is useful for validation and accuracy assessment of software tools for image registration, other image processing software that requires alignment of multimodal imaging data and accurate reference points, and tests of imaging hardware (resolution, sensitivity, radiation dose, etc.). The multimodal fiducial marker may be used on small animals, as well as other subjects, including humans. Still further advantages of the present invention will be appreciated to those of ordinary skill in the art upon reading and understanding the following detailed description.

The drawings are only for the purpose of illustrating preferred embodiments and are not to be construed as limiting the invention.

The fiducial marker of the present application is generally a multimodal fiducial marker for registration of different types of imaging data. The multimodal fiducial marker generally includes a first portion made from at least one radiopaque material and a second portion made from a porous material capable of absorbing at least one high density radioactive material. The second portion at least partially surrounds the first portion.

Figure 1:
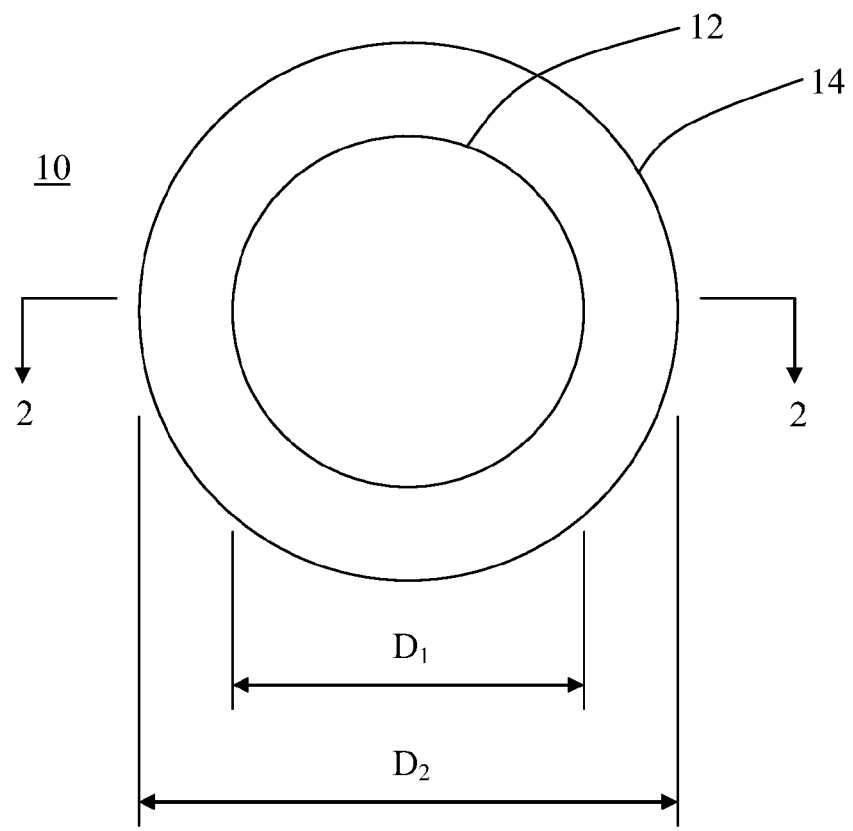
FIG. 1 is a top plan view of an exemplary fiducial marker according to an embodiment of the invention.
Figure 2:
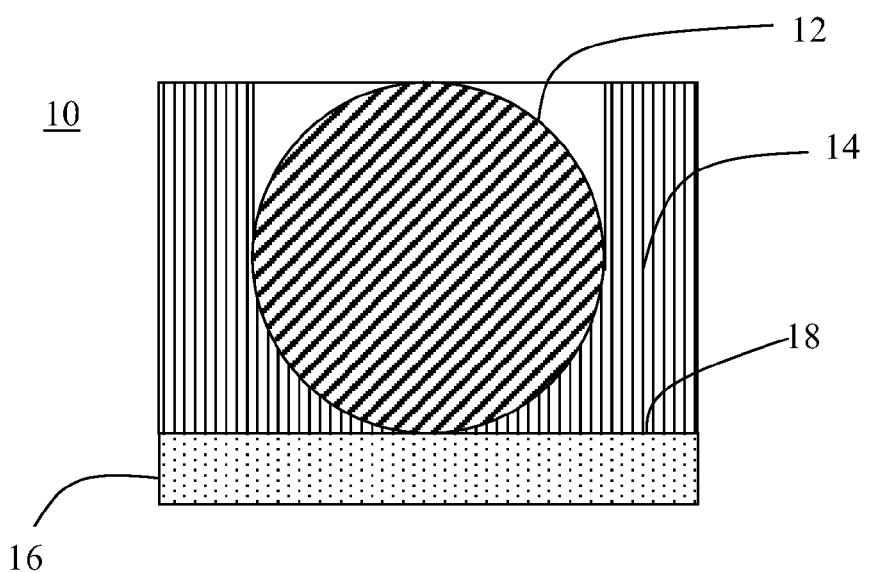
FIG. 2 is a cross sectional view taken along line 2-2 of FIG. 1.

More specifically, with reference to FIGS. 1 and 2, in an exemplary embodiment, the first portion 12 of a multimodal fiducial marker 10 is a radiopaque material. A radiopaque material is a material which is opaque to x-ray radiation, so it is visible in x-ray photographs and under fluoroscopy. Materials which are dense enough to be opaque to x-ray radiation are also typically visible in an ultrasound scan. Thus the first portion 12 will be visible to CT, fluoroscopy, and other x-ray based imaging systems, as well as ultrasound imaging systems.

The first portion 12 can be made for example from a metal, or from a non-metal material that is radiopaque, such as for example polyvinyl alcohol ("PVA"). The first portion 12 may also be made from a non-magnetic material, whether metal or non-metal, such as for example the metal aluminum. A non-magnetic first portion 12 may be preferred in some applications because it prohibits the magnetic field produced in a MR imaging system from moving the fiducial marker 10. In applications where registering an MR image with another image is desirable, the first portion 12 may be made of a non-magnetic material, such as for example, PVA or aluminum.

The first portion 12 of the exemplary fiducial marker 10 may be advantageously shaped in the form of a sphere, as shown for example in FIGS. 1 and 2. Such a spherical geometry allows the first portion 12 to be consistently identified from all angles and allows for accurate localization of the center of the fiducial marker 10. The spherical shape of the first portion 12 also allows the fiducial marker 10 to be easily detectable such that the image registration process may be automated. However, other shapes and geometries known in the art may be used. The first portion 12 may be hollow or solid.

The second portion 14 of the multimodal fiducial marker 10 is radioactive. For example, the second portion 14 may be comprised of a porous material which absorbs a radioactive material. Such a porous material may be for example paper, and is preferably hydrophilic paper. The radioactive material may be, for example, a liquid drop of 18F or 64Cu. Once the porous material is at least partially saturated with the radioactive material, the second portion 14 is activated. The resulting radioactivity of the second portion 14 will be visible to PET, micro PET, SPECT, and micro SPECT imaging systems.

As shown in FIGS. 1 and 2, the second portion 14 may at least partially surround the first portion 12, such that the first portion 12 is embedded in the second portion 14. Thus the second portion 14 may form a holder, or pouch, for the first portion 12. In some embodiments, the second portion 14 substantially surrounds the first portion 12.

The fiducial marker 10 shown in FIGS. 1 and 2 also includes an attachment means for attaching the fiducial marker 10 to the imaged subject, or an apparatus on or in which the imaged subject is disposed. The exemplary attachment means in FIGS. 1 and 2 comprises an adhesive layer 16 on a base 18 of the second portion 14, for attaching the fiducial marker 10 to a surface. However, the attachment means may be any suitable method known in the art capable of attaching the fiducial marker 10 to a surface, such as for example a suction cup, tape, screw, pin, staple, thread, tie, belt, clamp, cuff, elastic band, piercing, VELCRO®, or other fastener. The attachment means preferably allows the fiducial marker 10 to be detached and then reattached.

The size of a fiducial marker 10 constructed according to the present application will vary depending on numerous factors, including the type of scanners employed, the resolution of the scanners, and the size of the imaged subject. It is generally preferred that the overall size of the fiducial marker 10 be placed a small amount above the lower limit of the imaging system having the worst resolution. For example, the resolution of a PET system is typically on the order of 1 millimeter. If that is the worst resolution system being registered, then (as shown in FIG. 1) the diameter $D_1$ of the first portion 12 may be about 1.0 mm and the overall diameter $D_2$ of the multimodal fiducial marker 10 may be about 2.0 mm. Micro PET systems, by contrast, have resolutions on the order of several micrometers. If that is the worst resolution, then $D_1$ may be about 0.05 mm and $D_2$ may be about 1.0 mm. In most applications, a diameter $D_2$ will range from between about 0.05 mm and about 3.0 mm.

One exemplary method of using the multimodal fiducial marker 10 includes the step of placing one or more fiducial marker at a desired location on the subject to be scanned. The marker 10 may be attached to the subject, such as for example, with the adhesive layer 16 on the base 18 of the marker shown in FIGS. 1 and 2. Further, if the subject is to be scanned in a PET, micro PET, SPECT, or micro SPECT imaging system, a radioactive material, such as for example, a liquid drop of 18F or 64Cu, is placed on the second portion 14 of the fiducial marker 10. The second portion 14 absorbs the radioactive material and the resulting radioactivity allows the second portion to be visible in these and other imaging systems. The radioactive material may be placed on the second portion 14 before or after the fiducial marker 10 is placed on the subject to be scanned.

Once one or more fiducial markers 10 are placed at desired locations on the subject, scans may be taken using various different imaging modalities. The first portion 12 of the fiducial marker 10 will be visible in various modalities with or without radioactive material placed on the second portion 14, including CT, fluoroscopy, and other x-ray based imaging systems, as well as ultrasound imaging systems. As discussed, if the second portion 14 of the fiducial marker 10 is saturated with radioactive material, the second portion 14 will be visible in PET, micro PET, SPECT, micro SPECT, and perhaps other imaging systems. The complementary information, or data, provided by scans using any of these various modalities may be registered such that the acquired images are aligned in a common coordinate frame using the location of the multimodal fiducial marker 10 as a reference point or landmark.

Figure 3A:
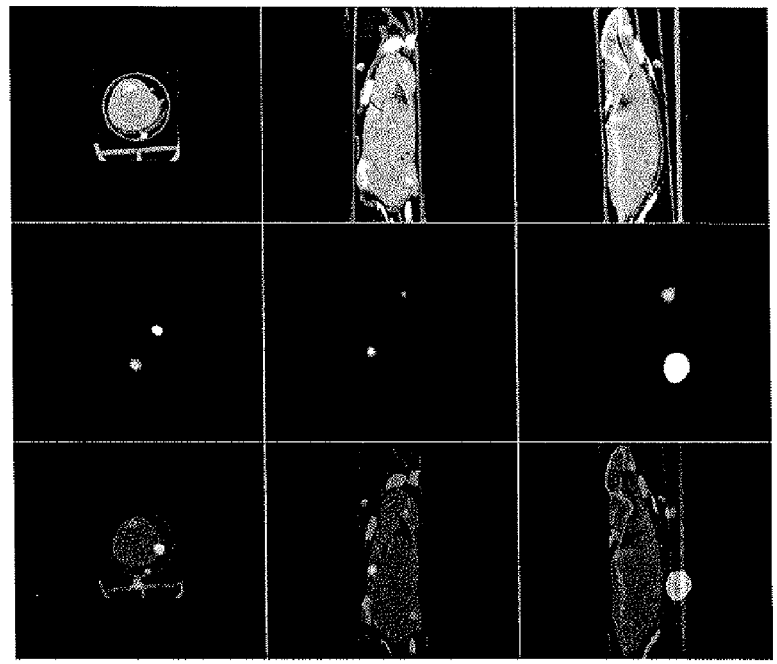
FIG. 3A shows CT and PET images of a mouse in a tube before image registration.
Figure 3B:
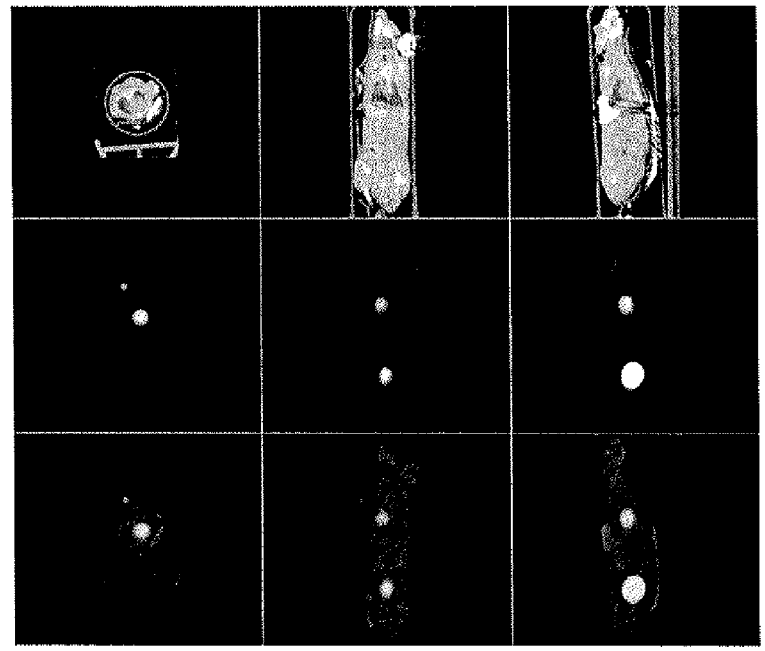
FIG. 3B shows CT and PET images of a mouse in a tube after image registration with an exemplary fiducial marker according to an embodiment of the invention.

FIGS. 3A and 3B show CT and PET images of a mouse in a tube before and after image registration with an exemplary fiducial marker according to an embodiment of the invention. As shown in FIG. 3A, the top row is a set of CT images, the middle row is a set of PET images, and the bottom row is a combination of the CT and PET images before fiducial registration. As shown in FIG. 3B, the top row is a set of CT images, the middle row is a set of PET images, and the bottom row is a combination of the CT and PET images after image registration with an exemplary fiducial marker according to an embodiment of the invention.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof. The invention may take form in various components and arrangements of components, and in various steps and arrangements of steps. The drawings are only for purposes of illustrating the preferred embodiments and are not to be construed as limiting the invention.

Having thus described the preferred embodiments, the invention is now claimed to be:

1. A multimodal fiducial marker for registration of multimodal data, comprising:
   a first portion comprising at least one radiopaque material; and
   a second portion comprising a radioactive material in combination with a porous component capable of absorbing the radioactive material;
   wherein the porous component of the second portion forms a cavity for receiving and supporting the first portion within the second portion.

2. The multimodal fiducial marker according to claim 1, wherein the second portion substantially surrounds the first portion.

3. The multimodal fiducial marker according to claim 1, wherein the fiducial marker is between about 0.05 and 3.00 mm in diameter.

4. The multimodal fiducial marker according to claim 1, wherein the fiducial marker is about 1.0 mm in diameter.

5. The multimodal fiducial marker according to claim 1, wherein the fiducial marker is identifiable in two or more of a CT, fluoroscopy, PET, micro PET, SPECT, micro SPECT, MR, or ultrasound scanner.

6. The multimodal fiducial marker according to claim 1 further comprising an attachment means for attaching the fiducial marker to a surface of a scanned subject.

7. The multimodal fiducial marker according to claim 1 further comprising a base having an adhesive for attaching the fiducial marker to a surface of a scanned subject.

8. The multimodal fiducial marker according to claim 1, wherein the first portion is spherical.

9. The multimodal fiducial marker according to claim 1, wherein the first portion is non-magnetic.

10. The multimodal fiducial marker according to claim 1, wherein the first portion comprises aluminum.

11. The multimodal fiducial marker according to claim 1, wherein the first portion comprises polyvinyl alcohol.

12. The multimodal fiducial marker according to claim 1, wherein the second portion comprises hydrophilic paper.

13. A multimodal fiducial marker for registration of multimodal data, comprising:
- a first portion comprising a radiopaque material, wherein the first portion is spherical; and
- a porous second portion comprising hydrophilic paper and capable of absorbing at least one radioactive material, wherein the second portion at least partially surrounds the first portion and defines a holder for the first portion.

* * * * *